United States Patent [19]

Shine

[11] Patent Number: 4,947,341
[45] Date of Patent: Aug. 7, 1990

[54] METHOD OF PREDICTING FATIGUE LIFETIMES OF METALLIC STRUCTURES

[75] Inventor: M. Carl Shine, Mountainvew, Calif.
[73] Assignee: Digital Equipment Corporation, Maynard, Mass.
[21] Appl. No.: 168,502
[22] Filed: Mar. 15, 1988
[51] Int. Cl.$^5$ ............................................. G01M 5/00
[52] U.S. Cl. .................................. 364/508; 364/506; 340/679; 340/665; 73/760; 73/763; 73/788
[58] Field of Search ................................. 364/506–508, 364/551.02; 340/679, 680, 665, 668; 73/760, 763, 788, 789, 791

[56] References Cited

U.S. PATENT DOCUMENTS

| | | | |
|---|---|---|---|
| 4,336,595 | 6/1982 | Adams et al. | 364/508 |
| 4,600,998 | 7/1986 | Huet | 364/507 |
| 4,656,595 | 4/1987 | Hognestad | 364/507 |
| 4,712,182 | 12/1987 | Wakamori et al. | 364/507 |
| 4,733,361 | 3/1988 | Krieser et al. | 364/506 |
| 4,758,964 | 7/1988 | Bittner et al. | 364/508 |

OTHER PUBLICATIONS

Halford, G. R. et al., "Life Prediction of Thermal-Mechanical Fatigue Using Strainrange Partitioning," in Thermal Fatigue of Materials and Components. ASTM STP 612 ASTM, Philadelphia, PA, 1976, pp. 239–254.
Halford, et al. "Temperature Effects on the Strainrange Partitioning Approach for Creep-Fatigue Analysis" NASA TMX-68023, 1972, pp. 1–19.
Moreno, V., et al. "Nonlinear Structural and Analyses Life of a Combustor Liner" MASA Tech. MEM 828946, 1982, pp. 1–16.
Shine, M. C. et al., "A Strain Range Partitioning Procedure for Solder Fatigue," IEPS vol. 4, Aug. 1985, pp. 11–14.
M. C. Shine et al. "Fatigue of Solder Joints in Surface Mount Devices," Proc. ASTM Symp on Low Cycle Fatigue, Oct. 1985.

*Primary Examiner*—Parshotam S. Lall
*Assistant Examiner*—Brian M. Mattson
*Attorney, Agent, or Firm*—Hayes, Soloway, Hennessey & Hage

[57] ABSTRACT

The lifetime NF (number of cycles to failure) of a metallic structure such as a soldered joint or the like is determined by three simple, rapid tests. The first is to determine creep displacement rate vs. load (stress). Next, from the same data, the slope of the matrix creep displacement vs. load (stress) curve is determined. A third test is to obtain load (stress) relaxation over a short period of time from a load (stress) in the matrix creep displacement region. The matrix creep displacement per cycle (CPS) is then derived by plotting matrix creep displacement rate vs. time and integrating the area under this curve. The number of cycles to failure (NF) is then calculated using the formula:

$$NF = \frac{\text{Creep Displacement to Failure}}{CPS}$$

6 Claims, 6 Drawing Sheets

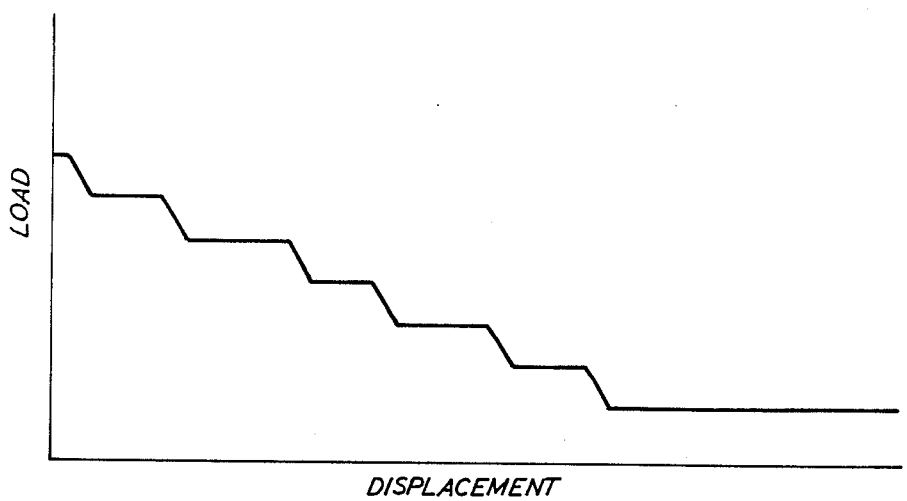

METHOD OF PREDICTING FATIGUE LIFETIMES OF METALLIC STRUCTURES

BACKGROUND OF THE INVENTION

When conducting research in the development of metallic structures, it is often highly desirable to compare various processing variables to determine their effect on the fatigue lifetime of the completed structure. Thus, methods of treatment of the structure, such as temperature of formation, subsequent heat treatment, alloy constituents, etc. are often compared to obtain an optimum structure. This is particularly true in research directed toward the development of metallic joints such as welded joints and, in particular, solder joints. While the present invention has broad applicability in the metallurgical field, it is of particular importance in the development of solder joints, more particularly those used in attaching various operative elements to a complex circuit board such as used in a computer.

The lifetime of any solder joint, particularly plastic leaded chip carrier solder joints, is of critical importance to the longterm operability of complex circuits which include large numbers of chips. This is particularly true when the joints, or the electronic instruments, e.g. computers, are used under conditions which may subject the joints to loads (stresses) at various times.

There are several methods now employed for testing these joints, most of which take days, months or even years to complete and yield unpredictable data. There are also some empirical formulations based on extrapolated Coffin-Manson plots. However, the results of these extrapolated test results are not related to actual use conditions, and there are no adequate mechanistic models to explain the failure mechanisms under the use conditions. Most methods employed today are related to leadless joints of high strains, not leaded joints of low strains and loads (stresses).

BRIEF SUMMARY OF THE INVENTION

In the present invention, the lifetime of a metallic structure, such as a solder joint, is tested to give an expected number of cycles to failure under anticipated conditions of use.

For simplicity of illustration, the invention will be initially described in connection with a preferred embodiment where leaded chip carrier solder joints are to be tested for comparison of various manufacturing parameters and their effect upon anticipated lifetime. In a preferred method of conducting the above procedure, actual displacement is used and actual load is used. While these can be reduced to absolute values, related to cross sectional area and thickness of a particular joint, it is not necessary when comparing one mechanical structure to an identical mechanical structure wherein the only change is the method of manufacturing, and the objective of the test is to determine which of the various methods of manufacturing is preferred from a fatigue lifetime standpoint. Accordingly, in the detailed description of the preferred form of the invention, actual displacement and actual loads are utilized rather than absolute displacement and absolute loads.

In a preferred form of the present invention, leaded chip carrier solder joints are tested using a standard Instron machine. It involves three simple, rapid tests. The first is to determine creep displacement rate versus load (stress). From the plotted results, the transition point from grain boundary creep displacement to matrix creep displacement is determined. Next, from the same data, the slope of the matrix creep displacement versus load (stress) curve is determined. The second test involves the determination of creep displacement to rupture in the matrix creep displacement region. The third test is to obtain load (stress) relaxation over a short period of time, such as ten minutes, from a load (stress) in the matrix creep displacement region. This test need be run only long enough to allow the creep displacement rate to drop by at least one order of magnitude. Thereafter, the matrix creep displacement per cycle (CPS) is derived by plotting matrix creep displacement rate versus time and integrating the area under this curve. Lastly, the number of cycles to failure (NF), which is an excellent indication of lifetime, is calculated by using the formula:

$$NF = \frac{\text{Creep Displacement to Failure}}{CPS}$$

DETAILED DESCRIPTION OF THE INVENTION

In order to more fully understand the present invention, reference should be had to the following specification in connection with the attached drawings, wherein:

FIG. 2 is a graph of a printout of the Instron machine showing displacement per unit of time as a function of load.

FIG. 3 is a graph of results from a number of tests on a solder joint over a wide range of loads to cover both the grain boundary and matrix creep displacement regions.

Figure 1:
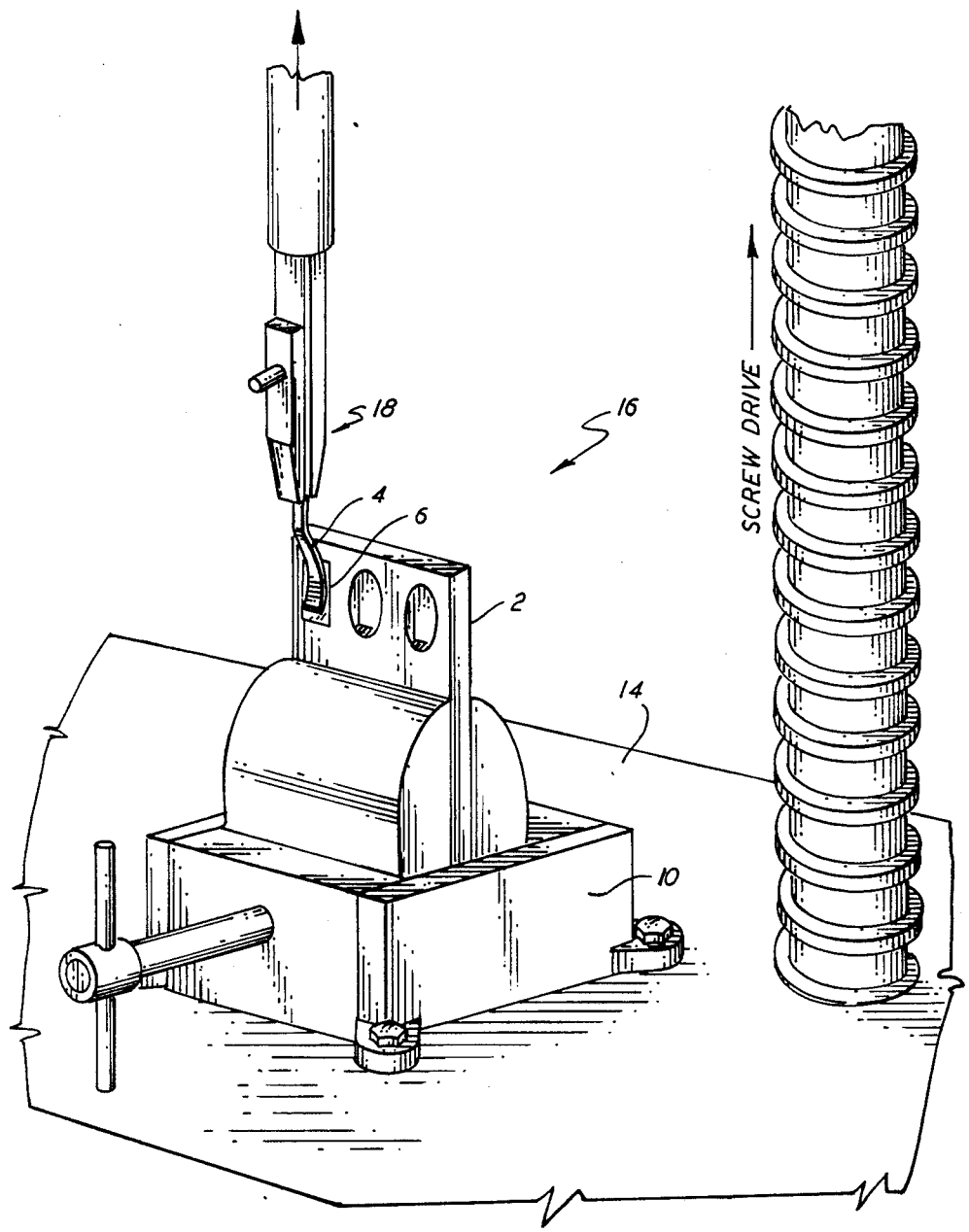
FIG. 1 is a schematic, diagrammatic drawing of a standard Instron test machine with a solder joint in position to be tested.

EXPERIMENTAL SET UP FOR TEST OF INDIVIDUAL SOLDER JOINT LEAD (J BEND, GULL WING, ETC.)

A. Isolate individual leads 4 by removing chip carrier from package.

B. Separate soldered lead contacts arrays into four separate quarters 2.

C. Machine off boards until within 10-15 mils of solder fillet 6.

D. Remove quadrant and grip in "Machinest" vice 10 which is bolted to base 14 of Instron machine 16 (See FIG. 1)

E. Bend up one lead of solder joint to test and straighten out to approximately 100 mils and clamp down on 100 mil lead area with special pin vice grip 18 attached to moving X-head of Instron machine (not shown in FIG. 1).

I. Instron Test Procedure to Obtain Creep Displacement Characteristic

A. Set Instron machine in load control mode. This is a standard procedure which uses a load control module which is an attachment accessory to any Instron machine, such as Model 1125, permitting a sample solder joint to be kept at constant load to within 1% with the creep displacement recorded on the Instron chart over a time interval which is recorded by pip marks.

B. Calibrate to hold at approximately 1 lb for a J bend shear.

C. Load up to 1 lb at 0.010 in./min. cross head speed; when load is reached, load control will hold at this value from previous set limits and solder joint will creep. Creep displacement is measured by chart displacement which is directly proportional to X-head motion. Reset cross head speed to 0.005 inches/min., and chart speed to 5 inch/min., which is equal to 0.001 inches displacement of the solder joint per inch of Instron chart. Time intervals are recorded by pip marks on the strain axis so that the creep displacement rate is calculated by dividing the creep displacement by the number of pips multiplied by the time per pip. The calculation is made over uniform pip spacings for the steady state creep condition. In FIG. 2, the pip time is 30 seconds.

D. Similarly for creep at 2 lbs., 3 lbs., 4 lbs., 5 lbs. per joint (see for example FIG. 2) with increasing creep loads, pip spacing increases because of increase in creep rates.

E. For the 1, 2, 3, 4, 5 lbs loads per joint plot, the creep displacement rates in mils/min. versus load (stress) in pounds; this gives the creep characteristic (FIG. 3). The creep characteristic consists of two branches; the grain boundary controlled branch which predominates at low loads (stresses) and creep displacement rates with a slope of 0.5–0.7, and the matrix controlled branch which predominates at high loads (stresses) and creep displacement rates with a slope of 0.15 (FIG. 3).

F. Using the creep displacement characteristic (FIG. 3), the matrix creep displacement rate versus load (stress) is obtained in the following manner. It is seen from FIG. 3 that a sharp transition occurs between the grain boundary controlled creep displacement region and the matrix controlled creep displacement region. If a dotted line is extended from the grain boundary controlled region (slope of 0.5–0.7), low loads (stresses) to the high loads (stresses) and creep displacement rates of the matrix region and the difference between this extrapolated line and the actual experimental data is plotted versus load (stress); this difference when plotted will represent the matrix creep displacement line which can be extrapolated to either lower or higher loads (stresses) to compute the matrix creep displacement in any arbitrary cycle (FIG. 3).

II. Instron Procedure to Obtain Creep Displacement Rupture

A. From creep displacement characteristic (FIG. 3), pick some load level which corresponds to a creep displacement rate well into the matrix controlled creep displacement region (approximately one order of magnitude higher creep displacement rate than the transition creep displacement rate : $3 \times 10^{-7}$ inch $SeC^{-1}$).

B. Set load control limits to creep at this value, 4 lbs sample, FIG. 4.

Figure 4:
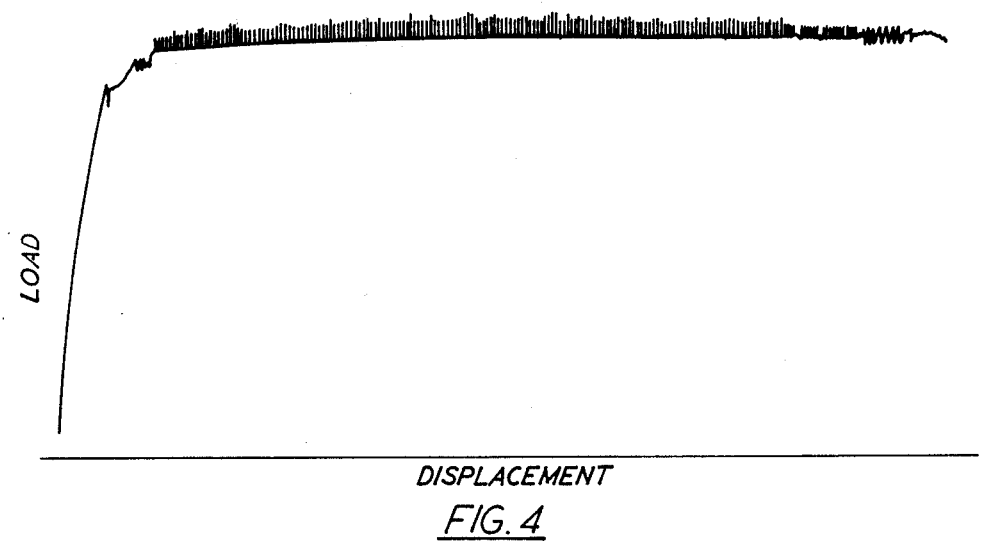
FIG. 4 is a graph of a printout of a test to rupture of a joint in the matrix creep displacement region.

C. Run creep test until rupture occurs (FIG. 4).

D. Total elongation due to creep over steady state creep region is creep displacement to rupture. The steady state creep displacement to rupture was 7.5 mils.

III. Instron Procedure to Determine Stress Relaxation Rates (Stress versus Time)

Figure 5:
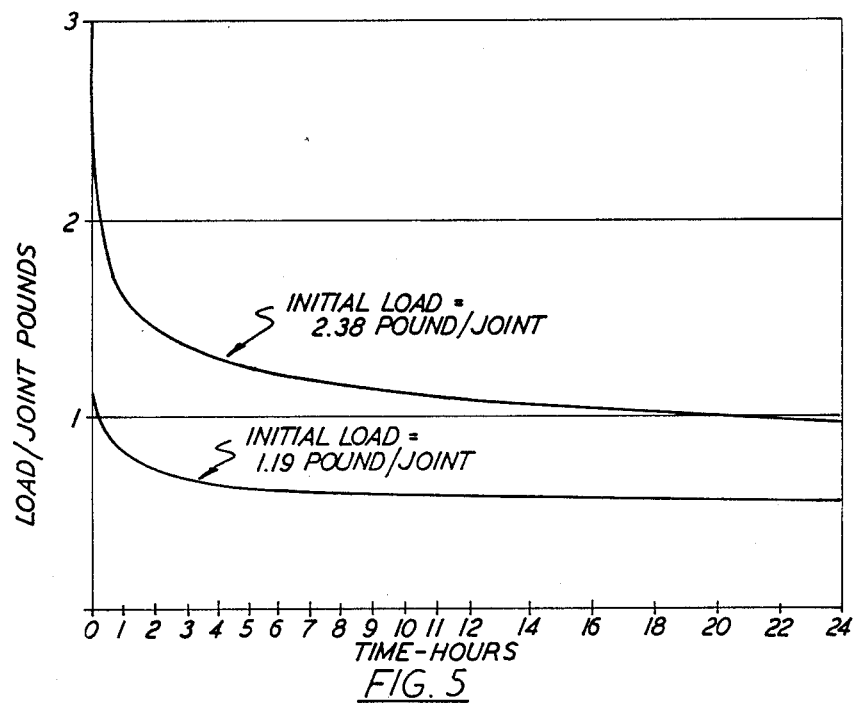
FIG. 5 is a graph of results of a load (stress) relaxation test.

A. Load up to 2.4 lbs. per lead (FIG. 5).

B. Allow load to relax for approximately 12 minutes recording the relaxation on the chart. This is the relevant load (stress) relaxation characteristic for the solder joint lifetime calculation using obtained data (FIG. 5), since in this 12 minute time period, the creep displacement rate has decreased by at least one order of magnitude.

IV. Procedure to Obtain Matrix Creep Displacement Rate Versus Time Profile

Figure 6:
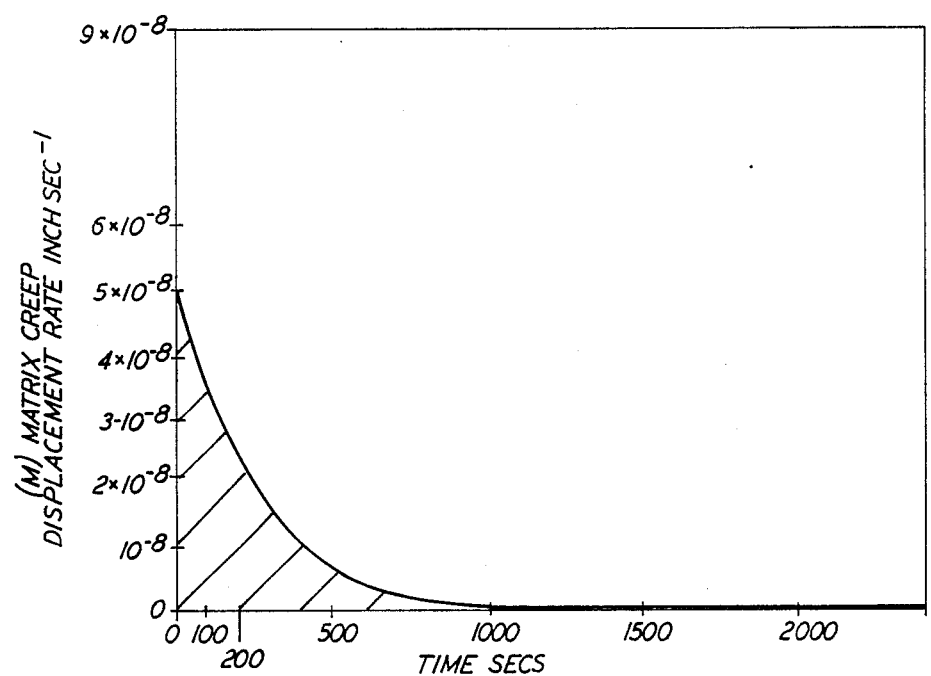
FIG. 6 is a graph of matrix creep displacement rate versus time.

A. Using the results of Section I F (above), load (stress) versus matrix creep displacement rate and FIG. 5, load (stress) relaxation versus time, creep displacement rate versus time is obtained over the relaxation cycle (FIG. 6 shows creep displacement rate versus time).

B. The area under this curve from time equals zero to time equals infinity equals the matrix creep displacement per cycle. Within 1% the integral can be evaluated over a time period of 12 minutes This is 0.012 mils in FIG. 6.

The number of cycles to failure for the measured load and temperature conditions obtained as above can then be calculated using the formula:

$$NF = \frac{\text{Creep Displacement to Rupture}}{CPS}$$

$$NF = \frac{7.5}{.012} = 625 \text{ cycles to failure}$$

SPECIFIC EXAMPLE

A junction on an 84I/O plcc made by a water vapor phase process was tested in accordance with the procedures outlined above in an Instron 1125. The composition of the solder joint was 63:37 tin lead. The joint had a cross section of $10-3$ in sq. and a thickness of 0.005 inch.

Creep Characteristics

The following data were obtained of various identical joints at the indicated loads.

| Load/Joint Pounds | Creep Rate mil/min |
|---|---|
| 1 | $42 \times 10^{-5}$ |
| 2 | $42 \times 10^{-2}$ |
| 3 | $24 \times$ |
| 4 | 600 |
| 5 | 3000 |

Creep Displacement to Rupture

The following data were obtained at 4 pounds/joint load.

Total steady state creep displacement was 0.0075 inch to rupture.

| Load/Joint Pounds | Stress relaxation Time (Seconds) |
| --- | --- |
| 2.38 | 0 |
| 2.2 | 360 |
| 1.9 | 720 |
| 1.7 | 2160 |
| 1.4 | 7200 |
| 1.2 | 28800 |

From the above data, curves corresponding to FIGS. 3 and 6 were prepared and the area under the matrix creep displacement rate versus time was integrated to obtain a value of 0.012 mils the matrix creep displacement per cycle.

The above method of testing solder joints can be used for screening different types of manufacturing processes and solder compositions used in making the joints to obtain quick evaluations of process variables and their effect on joint life. In other words, do they improve it or is there life degradation? The actual lifetime of a joint will, of course, depend upon the conditions of use of the joint. If a joint is to be used, for example, in a system employed in high performance aircraft where it is subjected sporadically to high G loadings, the maximum load (stress) on the joint can be measured (or calculated), and this maximum load (stress) can be utilized for obtaining the load (stress) relaxation curve data which can then be used with the matrix creep displacement rate to obtain a matrix creep displacement rate versus time curve which can be integrated to obtain the expected number of cycles to failure for that particular load on the joint. For example, if it is assumed that the number of cycles to failure is 600 and the joint is to be subjected to this load (stress) 100 times a year (i.e. on a fighter aircraft), the expected life of the joint would be six years. For other types of use, such as temperature cycles, which might give lower loads (stresses), and vibration which may give many, many loads (stresses) of lower value, these loads (stresses) can be actually measured or calculated. This will permit actual measurement of the stress relaxation curve at the anticipated maximum load in a particular cycle, and anticipated lifetime can then be calculated as above.

As can be seen, the invention provides a very quick and accurate qualitative test which enables the designer of a plastic leaded chip carrier joint to design solder composition and process variables which will provide an adequate joint for the anticipated use. Thus, when a joint is to be subjected to low loads (stresses), economies of manufacture, e.g. solder composition, or modified joint production techniques, can be employed, thus lowering the cost of the final product. On the other hand, where very high loads (stresses) are to be encountered, the performance characteristics of the joint, including solder alloy composition and manufacturing technology, can be optimized to give optimum performance of the joint under the anticipated loads.

As will he apparent from the above-description of the invention, it can be used as well with other types of joints such as other solder joints, welded joints, or even metallic structures which are subjected to different metallurgical treatments during the course of manufacture. With these other products, it is only necessary to measure actual displacements and displacement rates to obtain very quickly the displacement creep rate in the matrix creep region and the total displacement in the matrix creep region to rupture. The load (stress) relaxation rate can also be determined quickly over a very short period of time for stress relaxation and the number of cycles to failure for a particular structure can be calculated. This can then be compared for a number of other identical structures which have been formed under different metallurgical conditions, e.g. temperature alloy constituents, etc.

In order to demonstrate the use of the present invention to predict lifetimes for other metallic structures, published data is used on Hastelloy-x structures to calculate predicted lifetimes. These publications are:

(A) Halford et. al. "Temperature Effects on the Strain Range Partitioning Approach for Creep-Fatigue Analysis" NASA TMX-68023 1972, pp.17,18.

(B) Moreno, V., et al. "Nonlinear Structural an Life Analyses of a Combustor Liner" NASA TECH. MEM 82846, 1982.

EXAMPLE II

Location of Failure

The fatigue critical location of the combuster liner specimen is the edge of the louver lid. The observed failure mode is axial cracking from the edge toward the weld.

Estimation of the matrix creep from data and analysis is presented in the text.

Figure 7:
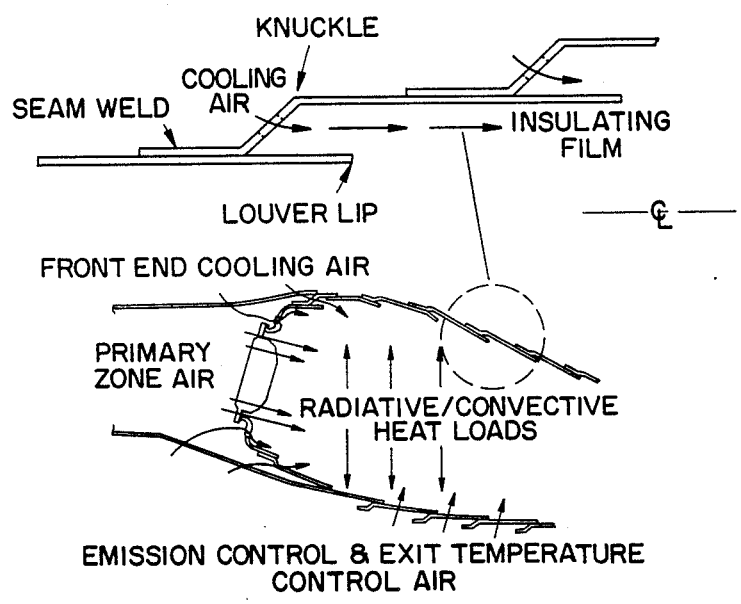
FIG. 7 is FIG. 1 of the Moreno et al reference.
Figure 8:
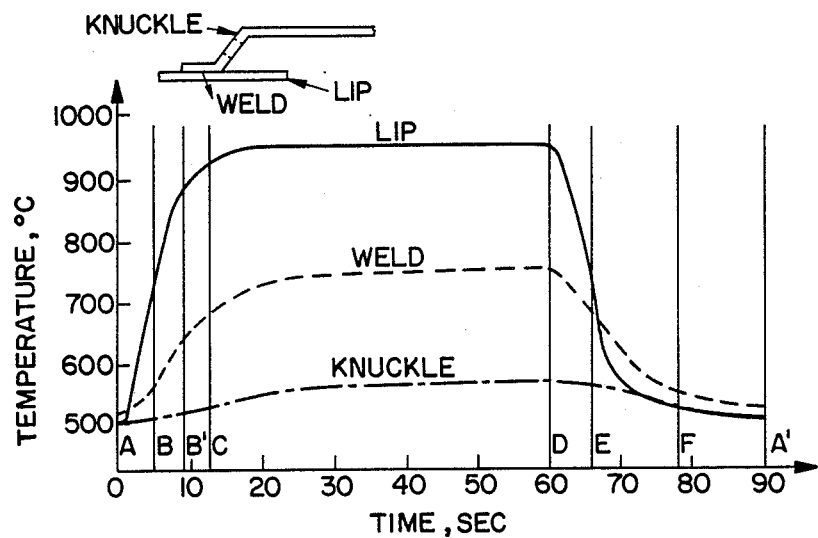
FIG. 8 is FIG. 2 of said Moreno et al reference.
Figure 9:
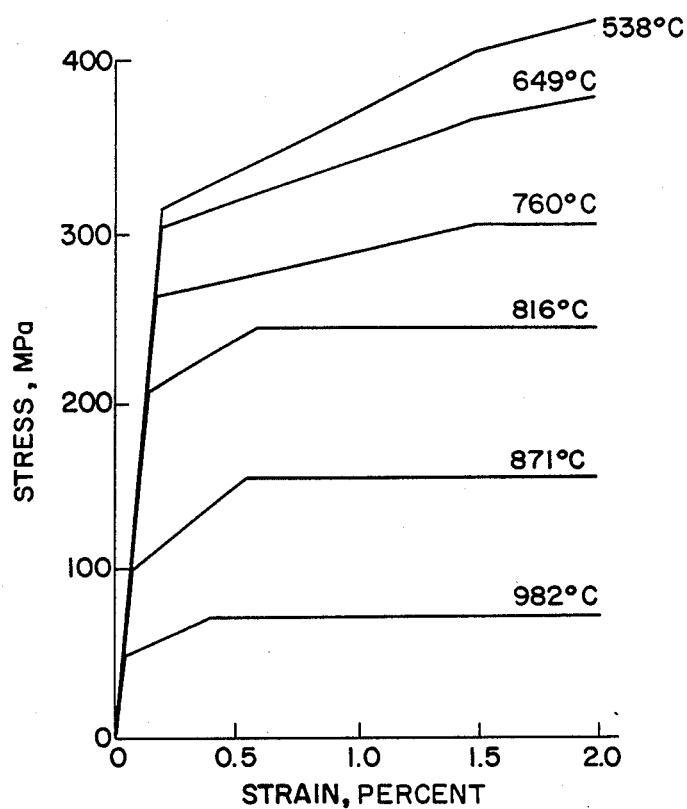
FIG. 9 is FIG. 3 of said Moreno et al reference.

In the Morena et al. article cited above, FIG. 1 (FIG. 7 herein) thereof shows the louver X section and FIG. 2 (FIG. 8 herein) the louver temperature response. FIG. 3 (FIG. 9 herein) shows that at the temperatures above 760 deg C. almost all the deformation is creep.

From the experimental data and the analysis and Table II (below), the authors estimated the inelastic strain to be 0.1% and the creep strain to be 0.0705%. Using the creep exponents from Table II to be a measure of the matrix creep and grain boundary creep; a value n=5.42 being associated with 100% matrix creep and a value n=2 being associated with 100% grain boundary creep, and assuming that the thermal cycle has a 40 sec dwell at approx. 940 deg. C. (n=3.5) (see FIG. 2 (FIG. 8 herein) of Reference B and Table II) the matrix creep per cycle is estimated to be ½x total creep=0.5×0.0705%=0.040%.

TABLE II

Temperature-Dependent Representation of Short-Time Hastelloy × Creep Response

| Temperature °C. | Constants for creep equation* $\epsilon cr = (\sigma/A)^n (t)$ | |
| --- | --- | --- |
| | A | n |
| 705 | 973 | 4.41 |
| 760 | 517 | 4.75 |
| 816 | 304 | 5.09 |
| 871 | 195 | 5.42 |
| 927 | 158 | 3.78 |
| 983 | 134 | 2.53 |

*Stress ($\sigma$)in MPa, creep strain rate ($\epsilon_{cr}$) in percent, (t) in hours.

TABLE III

Results of Combustor Liner Specimen Analyses (All results are for hoop direction at edge of louver lip)

| | Elastic | Inelastic (6th cycle) |
| --- | --- | --- |
| Max. strain, % | +.0135 | −.100 |
| Min. strain, % | −.361 | −.448 |
| Total strain range, % | .375 | .348 |
| Mean strain, % | −.174 | −.274 |
| Mean stress (MPa) | −245 | +138 |

TABLE IV

Tensile Ductility Data For Hastelloy X ½
Inch Thick Plate Versus Temperature (reduction in area)
(Date From Reference A)

| TEMPT deg C | RA (Percent) | Percent Elong = $100 \times \ln[100/(100-RA)]$ |
|---|---|---|
| 25 | 60 | 91 |
| 204 | 52 | 73 |
| 427 | 43 | 56 |
| 649 | 39 | 49 |
| 760 | 50 | 69 |
| 871 | 75 | 138 |

ESTIMATION OF THE MATRIX CREEP DUCTILITY FOR HASTX

Table IV shows the tensile(ductility of Hastx as a function of temperature. From FIG. 3 (FIG. 9 herein) in the text of Reference B, it is seen that most of the deformation is creep, at least from temperatures above 760 deg C. Therefore using a convenient temperature of 871 deg C. for which most of the creep is matrix creep because of the n=5.42 value (Table II) the matrix creep ductility can be estimated in the following way:

Total creep ductility at 871 deg C=138% (see Table IV above)

Since total creep=steady state creep+stage III creep and

Since steady state creep=stage III creep,

Therefore steady state creep=69%. Since most of steady state creep =matrix creep, we ban say that matrix creep ductility=69% (percent elongation in the steady state matrixcreep region).

The calculation of the lifetime of Hastx louver joint is set forth below:

Matrix creep ductility=69%
Matrix creep per cycle=0.04%

Lifetime in cycles = Matrix creep
doctility/matrix creep per cycle =
69/0.04 = 1725 cycles
Actual observed lifetime = 1000–1250 cycles
Calculation of lifetime by strain range
partitioning = 8000 cycles

I claim:

1. Method of determining lifetime Nf number of cycles to failure of a metallic structure which comprises the following steps:
    (a) measure displacement rate versus stress for the structure at a predetermined temperature,
    (b) determine transition between grain boundary creep displacement and matrix creep displacement from the measurements obtained in (a),
    (c) determine matrix creep displacement rate versus stress from the measurements obtained in (a),
    (d) measure amount of creep displacement to rupture (CDR) in a steady state matrix creep displacement region at said predetermined temperature,
    (e) measure stress relaxation over a time period from a predetermined initial stress in a matrix creep displacement region, this time being sufficiently long to permit creep rate to drop by at least one order of magnitude,
    (f) plot a creep displacement versus time curve from (c) and (e) above and calculate matrix creep displacement per cycle (CPS) by integrating area under said curve,
    (g) calculate number of cycles to failure (Nf) for the measured load and temperature conditions using the formula:

$$Nf = \frac{CDR}{CPS}.$$

2. Method of determining lifetime Nf number of cycles to failure of a metallic joint which comprises the following steps:
    (a) measure displacement rate versus stress for the joint at a predetermined temperature,
    (b) determine transition between grain boundary creep displacement and matrix creep displacement from the measurements obtained in (a),
    (c) determine matrix creep displacement rate versus stress from the measurements obtained in (a),
    (d) measure amount of creep displacement to rupture in a steady state matrix creep displacement region at said predetermined temperature,
    (e) measure stress relaxation over a time period from a predetermined initial stress in a matrix creep displacement region, this time being sufficiently long to permit creep rate to drop at lest one order of magnitude,
    (f) calculate matrix creep displacement per cycle (CPS) by integrating the area under a matrix creep displacement rate versus time curve plotted from (c) and (e),
    (g) convert the creep displacement to rupture to creep ductility (CD) by dividing displacement by initial thickness,
    (h) calculate number of cycles to failure (Nf) for measured load and temperature conditions using the formula:

$$Nf = \frac{CD}{CPS}.$$

3. Method of determining lifetime Nf number of cycles to failure of a solder joint which comprises the following steps:
    (a) measure displacement rate versus stress for the joint at a predetermined temperature,
    (b) determine transition between grain boundary creep displacement and matrix creep displacement from the measurements obtained in (a),
    (c) determine matrix creep displacement rate versus stress from the measurements obtained in (a),
    (d) measure amount of creep displacement to rupture (CDR) in a steady state matrix creep displacement region at said predetermined temperature,
    (e) measure stress relaxation over a time period from a predetermined initial stress in a matrix creep displacement region, this time being sufficiently long to permit creep rate to drop by at least one order of magnitude,
    (f) plot a creep displacement versus time curve from (c) and (e) above and calculate matrix creep displacement per cycle (CPS) by integrating area under this curve,
    (g) calculate number of cycles to failure (NF) for measured load and temperature conditions using the formula:

$$Nf = \frac{CDR}{CPS}.$$

4. Method of determining lifetime Nf number of cycles to failure of a solder joint which comprises the following steps:
 (a) measure displacement rate versus stress for the joint under predetermined temperature conditions,
 (b) determine transition between grain boundary creep displacement and matrix creep displacement from the measurements obtained in (a),
 (c) determine matrix creep displacement rate versus stress from the measurements obtained in (a),
 (d) measure amount of creep displacement to rupture (CDR) in a steady state matrix creep displacement region at said predetermined temperature conditions,
 (e) measure stress relaxation over a time period from a predetermined initial stress in a matrix creep displacement region, this time being sufficiently long to permit creep rate to drop by at least one order of magnitude,
 (f) plot a creep displacement versus time curve from (c) and (e) above and calculate matrix creep displacement per cycle (CPS) by integrating area under this curve,
 (g) calculate number of cycles to failure (Nf) for measured load and temperature conditions using the formula:

$$Nf = \frac{CDR}{CPS}.$$

5. In a method for optimizing processing variables affecting lifetime number of cycles to a failure of a solder joint which is subjected to cyclic stress and the solder joint has a failure mode due to creep having a grain boundary component and a matrix component, the improvement which comprises:
 A. prepare a group of solder joints under one set of processing variables:
  (a) measure displacement rate versus stress for one of said joints in a tensile test machine,
  (b) determine transition between grain boundary creep displacement and matrix creep displacement from the measurements obtained in (a),
  (c) determine creep displacement rate versus stress from the measurements obtained in (a),
  (d) measure amount of creep displacement to rupture in the steady state matrix creep displacement region of one of said joints in a tensile test machine,
  (e) in a tensile test machine, measure stress relaxation over a time period for a predetermined initial stress in the matrix creep displacement region for another of said joints, this time being sufficiently long to permit the creep rate to drop by at least one order of magnitude but less than the time necessary to complete relaxation,
  (f) plot a creep displacement versus time curve from (c) and (e) above and calculate matrix creep displacement per cycle by integrating area under this curve,
  (g) divide the creep displacement to rupture determined in (d) by the creep displacement per cycle determined in (f) to obtain the total number of cycles to failure;
 B. prepare one or more groups of solder joints under other sets of processing variables and repeat the steps (a) through (g) above with respect to each of said groups of solder joints to obtain values for number of cycles to failure for each said group; and
 C. pick that set of processing variables which provides a desired number of cycles to failure.

6. In a method for optimizing processing variables affecting lifetime number of cycles to failure of a metallic structure which is subjected to cyclic stress and the structure has a failure mode due to creep having a grain boundary component and a matrix component, the improvement which comprises:
 A. prepare a group of structures under one set of processing variables:
  (a) measure displacement rate versus stress for one of said structures in a tensile test machine,
  (b) determine transition between grain boundary creep displacement and matrix creep displacement from the measurements obtained in (a),
  (c) determine matrix creep displacement rate versus stress from the measurements obtained in (a),
  (d) measure amount of creep displacement to rupture in the steady state matrix creep displacement region in a tensile test machine,
  (e) in a tensile test machine, measure stress relaxation over a time period for a predetermined initial stress in a matrix creep displacement region, this time being sufficiently long to permit the creep rate to drop by at least one order of magnitude but less than the time necessary to complete relaxation,
  (f) plot a creep displacement versus time curve from (c) and (e) above and calculate matrix creep displacement per cycle by integrating area under this curve,
  (g) divide the creep displacement to rupture determined in (d) by the creep displacement per cycle deterimined in (f) to obtain the total number of cycles to failure;
 B. prepare one or more group of structures under other sets of processing variables and repeating the steps (a) through (g) above with respect to each of said groups of structures to obtain values for number of cycles to failure for each said group; and
 C. pick that set of processing variables which provides a desired number of cycles to failure.

* * * * *

UNITED STATES PATENT AND TRADEMARK OFFICE
CERTIFICATE OF CORRECTION

PATENT NO. : 4,947,341
DATED : August 7, 1990
INVENTOR(S) : M. Carl SHINE

It is certified that error appears in the above-identified patent and that said Letters Patent is hereby corrected as shown below:

In Claim 5 (c), Column 9, Line 44, --matrix-- should be inserted after "determine".

Signed and Sealed this

Twenty-seventh Day of August, 1991

Attest:

HARRY F. MANBECK, JR.

Attesting Officer

Commissioner of Patents and Trademarks